US012766366B2

(12) United States Patent
Ngai et al.

(10) Patent No.: US 12,766,366 B2
(45) Date of Patent: Oct. 20, 2026

(54) SYSTEM FOR PROVIDING GUIDED AND MONITORED EXERCISE ROUTINES

(71) Applicant: The Hong Kong Polytechnic University, Hung Hom (HK)

(72) Inventors: Pui Ching Shirley Ngai, Hung Hom (HK); Wui Man Lau, Hung Hom (HK); Man Hin Lam, Hung Hom (HK); Ching Hang Gabriel Fong, Hung Hom (HK); Ching Ching Cheung, Hung Hom (HK); Xiaoming Tao, Hung Hom (HK); Wai Hing Alex Choy, Hung Hom (HK); Yu-Keung Henry Chan, Hung Hom (HK); Wai Kwong David Man, Homantin (HK)

(73) Assignee: The Hong Kong Polytechnic University, Hung Hom (HK)

( * ) Notice: Subject to any disclaimer, the term of this patent is extended or adjusted under 35 U.S.C. 154(b) by 2 days.

(21) Appl. No.: 19/015,285

(22) Filed: Jan. 9, 2025

(65) Prior Publication Data

US 2026/0007930 A1 Jan. 8, 2026

Related U.S. Application Data

(60) Provisional application No. 63/667,003, filed on Jul. 2, 2024.

(51) Int. Cl.
*A63B 24/00* (2006.01)
*A61B 5/00* (2006.01)
(Continued)

(52) U.S. Cl.
CPC ........ *A63B 24/0084* (2013.01); *A61B 5/0022* (2013.01); *A61B 5/0077* (2013.01);
(Continued)

(58) Field of Classification Search
CPC ........... A63B 71/0622; A63B 24/0084; A63B 24/0062; A63B 24/0075; A61B 5/7246;
(Continued)

(56) References Cited

U.S. PATENT DOCUMENTS

2016/0086500 A1* 3/2016 Kaleal, III ............... A61B 5/20 434/257
2017/0000386 A1* 1/2017 Salamatian .......... A61B 5/6802
(Continued)

OTHER PUBLICATIONS

Lee, Y.J., Lee, M., Kim, N et al. Automatic Left and Right Lung Separation Using Free-Formed Surface Fitting on Volumetric Ct. J Digit Imaging 27, 538-547 (2014). https://doi.org/10.1007/s10278-014-9680-5 (Year: 2014).*

*Primary Examiner* — John D Li
(74) *Attorney, Agent, or Firm* — Stein IP, LLC

(57) ABSTRACT

A system for providing guided and monitored exercise routines wherein physiological data measurements are used to determine an optimized exercise program for a participant. The exercises are displayed on a smart device in such a way to maximize the benefits given the participant's current physiological state. Improvements including wellness monitoring and safety monitoring steps are also disclosed. In particular, measurements of total and individual lung performance and heart performance are used to select exercises and monitor health.

5 Claims, 5 Drawing Sheets

(51) Int. Cl.
*A61B 5/11* (2006.01)
*A61B 5/113* (2006.01)
*A63B 71/06* (2006.01)

(52) U.S. Cl.
CPC .......... *A61B 5/1102* (2013.01); *A61B 5/1128* (2013.01); *A61B 5/113* (2013.01); *A61B 5/7246* (2013.01); *A63B 71/0622* (2013.01); *A61B 2562/0261* (2013.01); *A61B 2562/164* (2013.01)

(58) Field of Classification Search
CPC ..... A61B 5/113; A61B 5/1128; A61B 5/1102; A61B 5/0077; A61B 5/0022; A61B 5/08; A61B 5/1118
See application file for complete search history.

(56) References Cited

U.S. PATENT DOCUMENTS

| | | | | |
|---|---|---|---|---|
| 2017/0367624 | A1* | 12/2017 | Nakazawa | G16H 50/30 |
| 2018/0110415 | A1* | 4/2018 | Sasahara | A61B 5/0008 |
| 2018/0129786 | A1* | 5/2018 | Khine | G16H 40/63 |
| 2018/0276823 | A1* | 9/2018 | Barral | A61B 5/7425 |
| 2022/0346703 | A1* | 11/2022 | Abdo | G16H 20/30 |

* cited by examiner

SYSTEM FOR PROVIDING GUIDED AND MONITORED EXERCISE ROUTINES

CROSS-REFERENCE TO RELATED APPLICATIONS

This application claims priority from and the benefit of U.S. Provisional Patent Application 63/667,003 filed Jul. 2, 2024 in the United States Patent & Trademark Office. All disclosures of the document(s) named above are incorporated herein by reference.

BACKGROUND OF THE INVENTION

1. Field of the Invention

Aspects of the invention relate to exercise routines for a participant guided and monitored by an external system, the external system having access to the participant's physiological state such as heart rate, respiratory rate, and other parameters as shall be shown herein.

2. Description of the Related Art

Various "smart" devices such as smart watches, smart mirrors, and smart exercise equipment can directly or indirectly measure the physiological conditions of participant while exercising. However, the existing format of exercise prescription via an online or app platform often has limited ability to prescribe or make exercise progression according to the participant's physiological responses (including but not limited to heart rate or respiratory rate).

This type of exercise prescription has substantial limitations in tailoring the exercise type and level of difficulty (or exercise intensity) according to the condition of the participants, which reduces its benefits. A system for evaluating the condition of the participants and adjusting the exercise type and level of difficulty or intensity would be a useful invention.

Such exercise prescription can also pose safety risk to the participants as there is no monitoring of their performance and physiological responses. A system for evaluating the condition of the participants for health and safety issues during exercise would be a useful invention.

As respiratory infections and conditions which can affect lung health and efficiency are now a common and serious health and safety issue, a system for monitoring lung health and efficiency over time would also be a useful invention.

Aspects of the present invention address these concerns.

SUMMARY OF THE INVENTION

Aspects of the present invention comprise a system using a collection of medical sensors and a smart device which receives data from these sensors to both evaluate the physiological condition of a participant using the system and design, implement, and guide the participant through exercises suitable for their condition while monitoring the participant for any irregularities or health and safety issues during the exercises. In particular, volumetric evaluations of lung efficiency and consistency can be monitored with the system.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1:
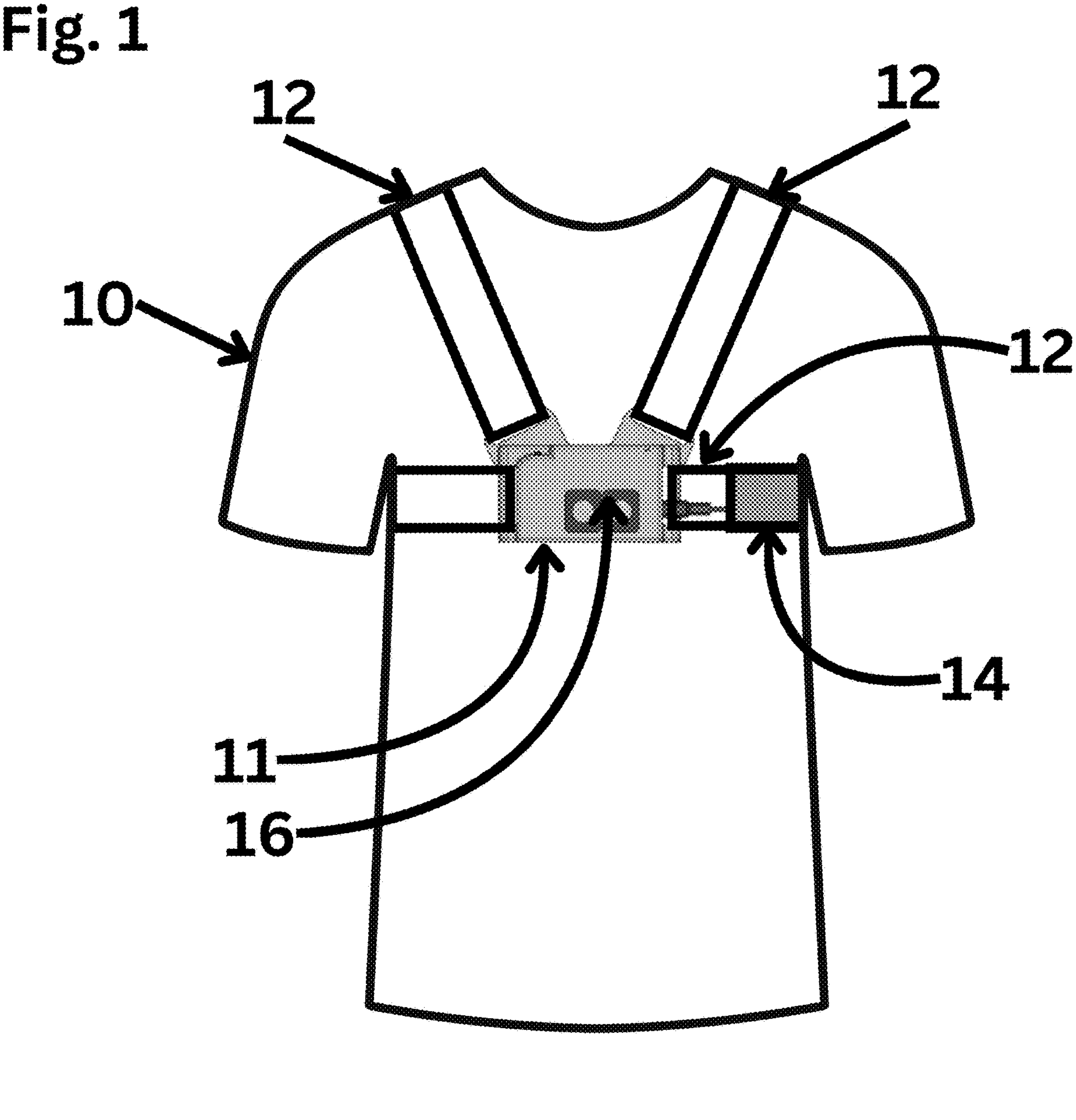
FIG. 1 is a front view of a device for use with the system of the invention.

Reference will now be made in detail to several embodiments of the invention that are illustrated in accompanying drawings. Whenever possible, the same or similar reference numerals are used in the drawings and the description to refer to the same or like parts or steps. The drawings are in simplified form and are not to precise scale. For purposes of convenience and clarity only, directional terms such as top, bottom, left, right, up, down, over, above, below, beneath, rear, and front, can be used with respect to the drawings. These and similar directional terms are not to be construed to limit the scope of the invention in any manner. The words attach, connect, couple, and similar terms with their inflectional morphemes do not necessarily denote direct or intermediate connections, but can also include connections through mediate elements or devices.

Figure 2:
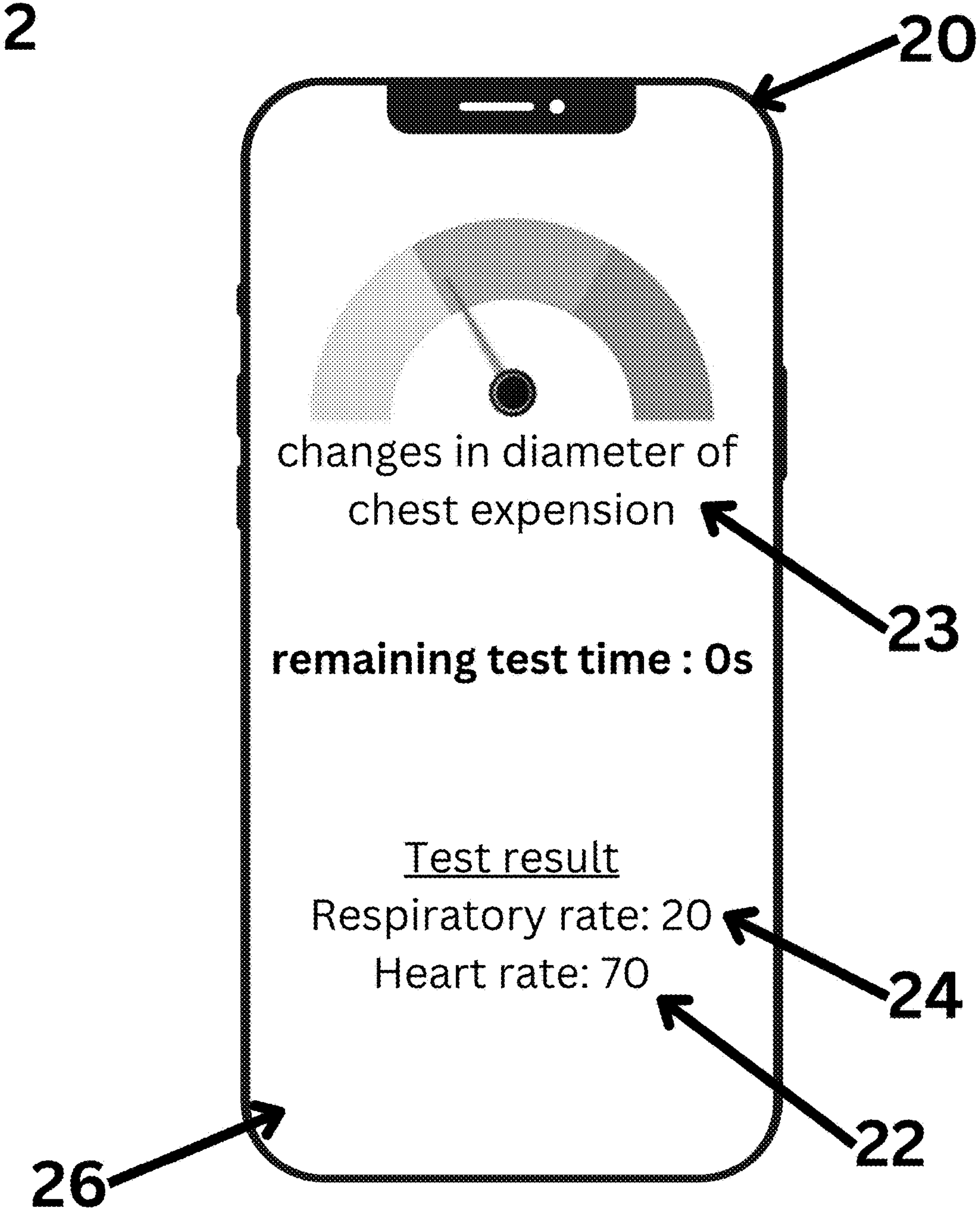
FIG. 2 is a front view of a smartphone being used in association with the system of the invention.
Figure 5:
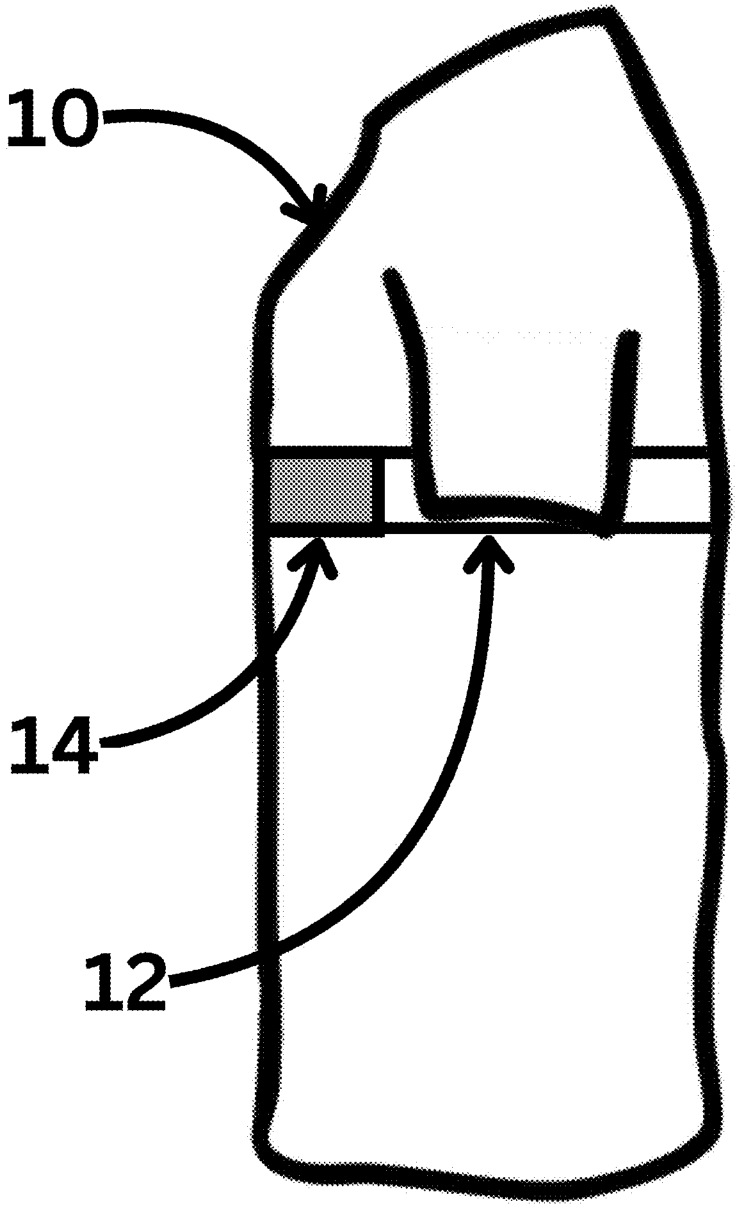
FIG. 5 is a side view of a device for use with the system of the invention and comprises the view of FIG. 1 rotated 90 degrees along a vertical axis.

By referring to FIGS. 1, 2, and 5, the basic principle of the invention can be easily understood. FIG. 1 shows the torso of a participant wearing a device, referred to as a "sensor rig" for purposes of this specification, used to take the measurements required by the system. Participant 10 is wearing sensor rig 11, which comprises straps 12, chest expansion sensors 14, and control unit 16.

Control unit 16 can incorporate and/or be connected to additional sensors (NOT SHOWN) including but not limited to: a heart rate monitoring device, and/or any other appropriate or desired sensors. Sensors may also be incorporated into the system by wired or wireless connection to smart device 20 (see FIG. 2.)

A first example of an additional sensor includes a camera-based heart rate measurement device. This uses an optical sensor such as the camera of a smart phone which can be incorporated into smart device 20 or a separate camera connected wirelessly or by wire to the system.

A second example of an additional sensor includes a heart rate monitoring through smart watch connected wirelessly to the system. This can monitor heart rate changes of the participant during a performed exercise.

A third example of an additional sensor includes a position-based lung performance measurement device as shown in FIG. 5. This can use a sensor or sensors 14 on straps 12 which can detect their relative position in space which move as the participant breathes in and out, or alternatively sensors which detect an elastic strain, with either detected measurement corresponding to the extent of the expansion and contraction of the lungs. From these measurements a respiratory rate measurement can be determined.

Many other examples of additional sensors are possible. Traditional physiological sensors and their incorporation should be apparent to those of ordinary skill in the art. Other sensors can be developed specifically for this application or as novel sensors which can then be used in a variety of applications.

Control unit 16 includes a wireless send/receive device such as a Bluetooth® transceiver, a proprietary wireless transceiver, and/or any other appropriate or desired send/receive device. Physiological state data is gathered by sensor rig 11 and transmitted to smart device 20. Straps 12 are optional, though some reasonable means for attaching sensor rig 11 to the participant is useful. The sensors can be integrated directly into control unit 16 or connected to control unit 16 by wire or wirelessly. A power source (not shown) such as a disposable or rechargeable battery is also required, but any appropriate source(s) would be familiar to those of ordinary skill in the art and so are not further described or specified.

As shown in FIG. 2, smart device 20 receives the data from sensor rig 11 and uses it to provide the guided and monitored exercise routines made possible by the invention. (See FIG. 3.) Smart device 20 may comprise a cell phone, a tablet computer, a laptop, a desktop computer, a smart watch, or any other appropriate or desired device. In the embodiment described herein, sensor rig 11 uses data from chest expansion sensors 14 to not only display the respiratory rate of the participant and display it on display 26, e.g. as respiratory rate readout 24, but by using multiple sensors, it can display heart rate 22 and the diameter changes of chest expansion 23.

It is also possible to use one or more sensors built into the smart device, such as an accelerometer, gyroscope, step sensor, et cetera, in connection with the invention. While the description of the embodiment will assume that all sensors are incorporated into the sensor rig, aspects of the invention will work equally well using such smart device sensors as a component of the overall system.

Figure 3:
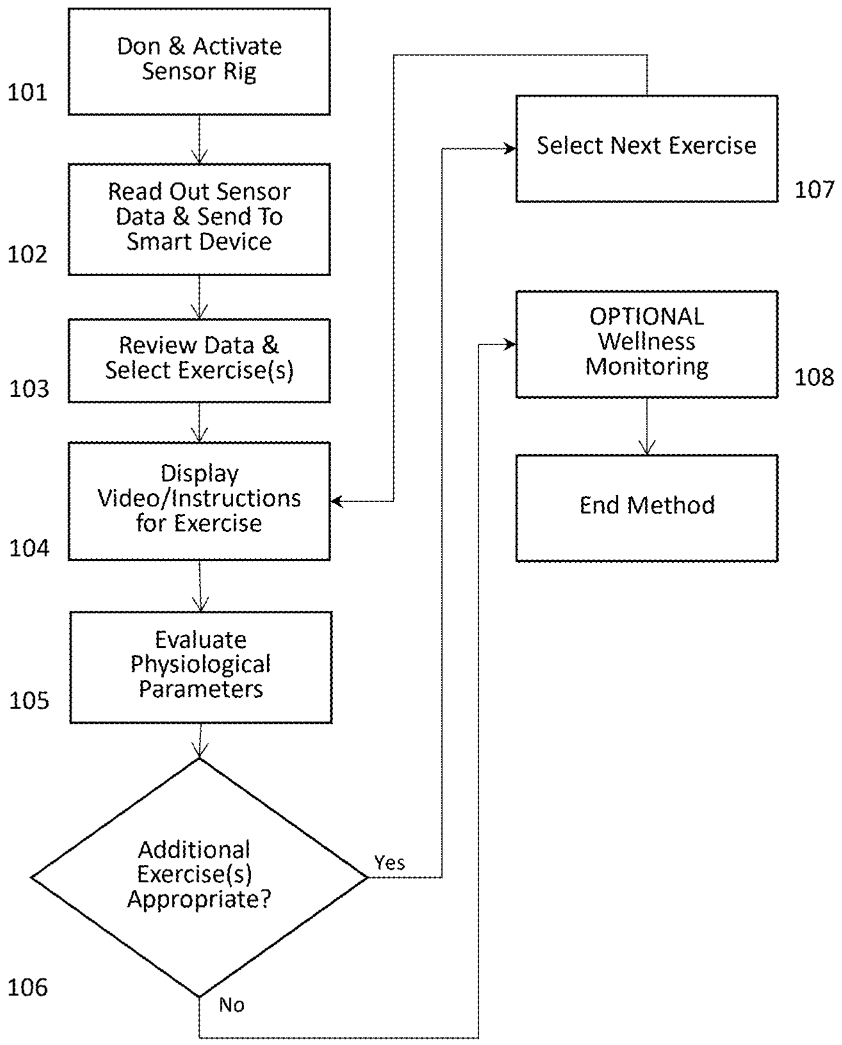
FIG. 3 is a flow chart of the operation of the system of the invention.

FIG. 3 shows a sequence of operation of the system according to an aspect of the invention. In Step 101, the participant dons and activates the sensor rig 11, including powering the sensor rig 11 on, powering the smart device 20 on if needed, linking the sensor rig 11 to the smart device 20 if needed, and observing the smart device 20 to wait for an indication that the smart device 20 is receiving data from the sensor rig 11.

In Step 102, the sensor rig 11 reads out the current parameters for all sensors present and activated. If motion or other activity is necessary on the part of the participant, the smart device 20 displays instructions and/or examples. For instance, if the common "sit to stand" exercise is used to measure one or more parameters, the smart device 20 will indicate to the participant to sit down and stand up one or more times, including an optional display of a video of a person performing the desired action(s.) An accelerometer on smart device 20 and/or on sensor rig 11 can detect the speed and smoothness of the performed exercise. A gyroscope on smart device 20 and/or on sensor rig 11 can also measure the amount of tilt or sway the participant displays when performing an exercise.

In Step 103, the smart device 20 and/or the sensor rig 11 executes a program (see FIG. 4) which collates the data gathered in Step 102 and correlates it against other known parameters of the participant such as their age, past medical history, etc., to determine an appropriate set of one or more exercises tailored for maximum efficiency in improving the participant's health while remaining safely within their capabilities. The program can be configured to emphasize one or more parameters as appropriate. As an example, if the participant's heart rate is suboptimal, the program can select an exercise or exercises meant to improve pulmonary function and capacity. The program integrates the assessment results, physiological data and subjective exertion collected for the prescription of exercise, including a combination of warm-up, breathing exercise, strengthening exercise, aerobic exercises, and stretching exercises as appropriate. The first exercise selected becomes a current exercise.

In Step 104, the current exercise is displayed on the smart device 20 with text, audio, and/or video prompting to allow the participant to most effectively perform the exercise for maximum efficiency and benefits.

In Step 105, after each exercise component, respiratory rate, heart rate, and other physiological parameters of the participant are measured to decide the progression of the exercise routine using a custom algorithm.

In Step 106, if additional exercises are determined to be appropriate by the program, a next exercise is selected as the current exercise in Step 107 as determined by the custom algorithm, otherwise the operating sequence is complete.

In Step 107, the operating sequence loops to Step 104 with the current exercise, and the sequence repeats Steps 104 to 106.

In optional wellness monitoring step 108, some or all of the data gathered during the operation of the system of the invention is directly transmitted and/or stored for later transmission or review to health professionals. For instance, if the participant's respiratory rate has increased after exercising as determined by the individual chest expansion sensors, a physician can be notified and further diagnostic procedures initiated.

An optional safety monitoring step 109 (NOT SHOWN) can also be executed during operation of the system. If any particular physiological parameter measured by sensor rig 11 leaves a defined safe range, including but not limited to unsafe heart rate, lung expansion, or body temperature the system responds appropriately. This step is performed as frequently as desired, either between other measurements and evaluations or concurrently with the same data. If an unsafe condition is detected, the smart device 20 pauses or halts the exercise program until the unsafe condition ceases. It is optional to have the sensor rig 11 continue to monitor the physiological data and resume the operating sequence once all parameters return to a safe range.

Figure 4:
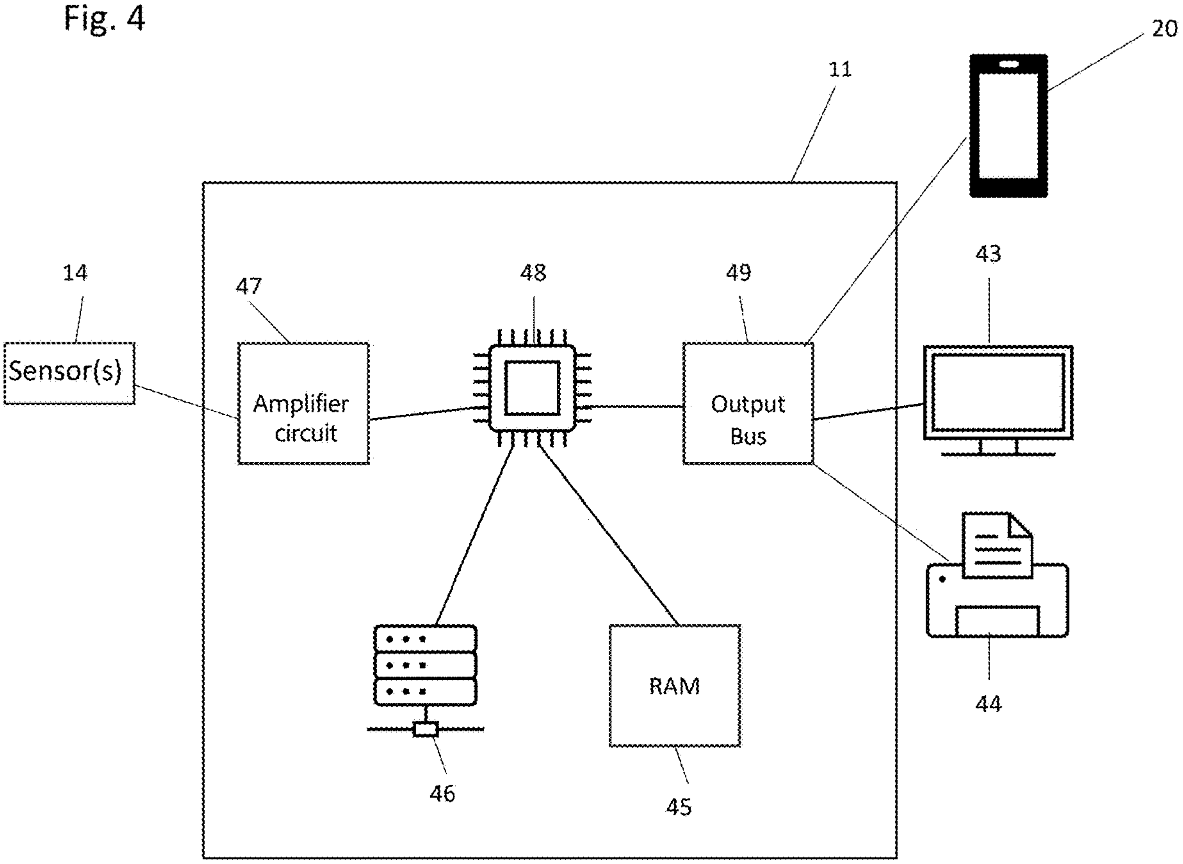
FIG. 4 is an abstract schematic of the device for use with the system of the invention.

FIG. 4 shows an abstract schematic for the device used to implement the system. Sensor rig 11 comprises a central processing unit or CPU 48, a persistent storage 46, a random access memory or RAM 45, an amplifier circuit 47, and an output bus 49. Sensor(s) such as sensor 14 are connected to sensor rig 11 and then amplified by the amplifier circuit 47. Amplifier circuit 47 sends the sensor data to CPU 48, which processes it appropriately and stores it in RAM 45 and/or persistent storage 46 as directed by control code stored in persistent storage 46. Persistent storage 46 can comprise a solid state drive or SSD, a hard disk drive or HDD, flash storage, or any other reasonable and appropriate storage means.

Smart device 20, here a smartphone, has a communications connection to output bus 49. This can be wired or wireless as set forth above. The program which enables the system to function can be stored as an app on smart device 20 and/or in the persistent storage and/or RAM of sensor rig 11.

Any portion of the program stored on smart device 20 is executed by it on the data received from sensor rig 11. It is optional to also send the data to a printer 44, a separate display 43, or a cloud-based transmission system (NOT SHOWN) as would be apparent to a person of ordinary skill in the art. The data, the evaluation of the data, and the exercises to be performed are then displayed on the display of smart device 20 and/or separate display 43. The data, the evaluation, and/or instructions for the exercise(s) can also be printed on printer 44.

Proper application of geometry can also allow a third chest expansion sensor or, alternatively, a second and third chest expansion sensor (NOT SHOWN) each paired to the chest expansion sensor 14 shown in FIG. 1 and FIG. 5, to measure the absolute expansion of the participant's lungs and therefrom an absolute change of respiratory rate.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A system for providing guided and monitored exercise routines comprising:

a) a sensor rig configured to be worn on a torso of a participant, the sensor rig comprising a processor, a memory, a wireless transceiver, and a plurality of chest expansion sensors disposed at different positions about the torso, each of the plurality of chest expansion sensors configured to detect a respective chest expansion movement of the participant while breathing;

b) the sensor rig configured to collect, from the plurality of chest expansion sensors, a plurality of chest expansion measurements and to derive therefrom a pulmonary data measurement representing an absolute expansion of the participant's lungs, wherein the plurality of chest expansion sensors are positioned to permit geometric determination of the absolute expansion of the participant's lungs from the plurality of chest expansion measurements;

c) a smart device which receives the pulmonary data measurement from the sensor rig via the wireless transceiver;

d) a program code stored on the smart device which uses the pulmonary data measurement to select at least one targeted exercise for the participant;

e) a display operably connected to the smart device which displays the targeted exercise to the participant such that the participant can follow along and perform the targeted exercise; and f) wherein the program code is configured to:

(i) receive the pulmonary data measurement from the sensor rig;

(ii) compares the pulmonary data measurement with a correlated safety limit;

(iii) automatically suspend presentation of the targeted exercise on the display when the pulmonary data measurement exceeds the correlated safety limit;

(iv) continue comparing pulmonary data measurements subsequently received from the sensor rig with the correlated safety limit while presentation of the targeted exercise remains suspended; and (v) automatically resumes presentation of the targeted exercise on the display after one of the pulmonary data measurements subsequently received from the sensor rig is determined to be within the correlated safety limit.

2. The system of claim 1, wherein each of the plurality of chest expansion sensors detects at least one of a relative position in space and an elastic strain corresponding to the chest expansion movement.

3. The system of claim 1, wherein the smart device records the pulmonary data measurement to create a recorded physiological data measurement.

4. The system of claim 3, wherein the recorded physiological data measurement is transmitted to a health care professional for evaluation.

5. The system of claim 1, wherein the smart device transmits an alert to at least one third party recipient if the pulmonary data measurement exceeds the correlated safety limit by a predetermined danger level.

* * * * *